(12) United States Patent
Koch

(10) Patent No.: US 6,571,622 B2
(45) Date of Patent: Jun. 3, 2003

(54) COMBINED RESPIRATORY FLOW SENSOR

(75) Inventor: Jochim Koch, Ratzeburg (DE)

(73) Assignee: Dräger Medical AG & Co. KGAA (DE)

( * ) Notice: Subject to any disclaimer, the term of this patent is extended or adjusted under 35 U.S.C. 154(b) by 0 days.

(21) Appl. No.: 10/032,934

(22) Filed: Dec. 26, 2001

(65) Prior Publication Data

US 2002/0108437 A1 Aug. 15, 2002

(30) Foreign Application Priority Data

Feb. 9, 2001 (DE) .......................... 101 06 046

(51) Int. Cl.⁷ ............................................ G01F 1/68
(52) U.S. Cl. .................................................. 73/204.11
(58) Field of Search ...................... 73/864.63, 863.71, 73/864.64, 204.11, 204; 250/343; 600/529–538

(56) References Cited

U.S. PATENT DOCUMENTS

| | | | | |
|---|---|---|---|---|
| 4,300,391 A | * | 11/1981 | Eiermann | ............... 73/204.26 |
| 4,314,564 A | | 2/1982 | Albarda | |
| 5,834,777 A | * | 11/1998 | Wong | ..................... 250/338.4 |
| 6,142,024 A | * | 11/2000 | Rauleder et al. | ........... 250/428 |
| 6,271,043 B1 | * | 8/2001 | Godec et al. | ............... 422/100 |

FOREIGN PATENT DOCUMENTS

| | | |
|---|---|---|
| DE | 29 06 790 A1 | 8/1980 |
| DE | 197 16 061 C1 | 3/1998 |

* cited by examiner

*Primary Examiner*—Harshad Patel
*Assistant Examiner*—Jewel V. Thompson
(74) *Attorney, Agent, or Firm*—McGlew and Tuttle, P.C.

(57) ABSTRACT

A compact, one-part respiratory flow sensor with a small dead space volume for the simultaneous measurement of both the gas volume flow and the concentration of gas components of the respiratory flow. The respiratory flow sensor has a tubular housing (1) with two opposite windows (2, 3) which are arranged at right angles to the direction of flow and limit the respiratory flow and are formed of a material transparent to infrared radiation. An infrared sensor with an infrared radiation source (4) and with at least one infrared radiation detector (5) is connected to the housing (1). The infrared radiation source (4) irradiates one of the two windows (2, 3) of the housing (1). The infrared radiation detector (5), of which there is at least one, receives the infrared radiation of the infrared radiation source (4) after its passage through the respiratory flow and the two windows (2, 3) limiting the respiratory flow. At least one measuring transducer for the gas volume flow is arranged in the tubular housing (1) outside the beam path of the infrared radiation.

12 Claims, 1 Drawing Sheet

COMBINED RESPIRATORY FLOW SENSOR

FIELD OF THE INVENTION

The present invention pertains to a respiratory flow sensor for the measurement of the gas volume flow and the concentration of gas components in the respiratory flow and more particularly to a flow sensor with a generally tubular housing with two opposite windows of a material transparent to infrared radiation, arranged at right angles to the direction of flow, and an infrared sensor with an infrared radiation source and with at least one infrared radiation detector with the infrared radiation source irradiating one of the two windows of the housing and with the infrared radiation detector receiving the infrared radiation of the infrared radiation source after the radiation has passed through the respiratory flow and the two windows and at least one measuring transducer for the gas volume flow, which is arranged in the tubular housing outside the beam path of the infrared radiation.

BACKGROUND OF THE INVENTION

Both measuring means for determining the gas volume flow and for determining the concentration of gas components of the respiratory flow of patients have been known as separate measuring units in clinical practice. Infrared measurement methods, in which radiation is sent through the gas volume flow, e.g., the method described in DE 197 16 061 C1, are preferably used for the measurement of the concentration of gas components in the respiratory flow, wherein the concentration-dependent absorption of the infrared radiation emitted by an infrared radiation source is determined by means of suitable infrared radiation detectors after the radiation has passed through a measured gas cuvette, for a wavelength characteristic of a certain gas such as $CO_2$. The concentration of the given gas can be determined by calculation from the measured signal received.

A sensor for the measurement of the gas volume flow and a separate sensor for the measurement of the concentration of gas components, each in a separate housing, have hitherto been connected in series for special tests (FRC, Functional Residual Capacity of the lungs). This practice is complicated in terms of handling, the overall arrangement is relatively bulky and, in particular, such a conventional arrangement for the measurement of the concentration of gas components of the respiratory flow of patients is subject to errors, which can be attributed to the relatively large volume of the dead space of the series-connected overall arrangement. The size of the volume of the dead space has a considerable effect on the $CO_2$ values of the patient especially in the case of the respiration of premature and newborn patients. Thus, an increase in the volume of the dead space from 1 to 2.5 mL leads to an increase in the $CO_2$ measured in the blood by about 30%, i.e., the mechanical respiration must be adjusted by correspondingly increasing the respiration volume supplied or the respiration pressure. These measures may in turn lead to a considerable stress for the patient, especially to an overexpansion of the lungs with irreparable damage to the lungs. On the other hand, it is desirable to measure and monitor important characteristics, especially the $CO_2$ content in the air breathed out as well as the instantaneous and maximum gas volume flow and the respiratory volume determined by integration over one breath, with the shortest possible time delay during the mechanical respiration of the patients. The gas volume flow can be determined with sensors that are known per se, e.g., with hot wire anemometers or with mechanical measuring transducers.

SUMMARY AND OBJECTS OF THE INVENTION

The object of the present invention is consequently to provide a combined and compact respiratory flow sensor, which is suitable for the simultaneous measurement of both the gas volume flow and the concentration of gas components of the respiratory flow.

According to the invention a respiratory flow sensor is provided for the measurement of the gas volume flow and the concentration of gas components of the respiratory flow. The respiratory flow sensor has a tubular housing with two opposite windows arranged at right angles to the direction of flow and consist of a material transparent to infrared radiation. An infrared sensor with an infrared radiation source and with least one the infrared radiation detector is connected to the housing. The infrared radiation source irradiates one of the two windows of the housing. The infrared radiation detector receives the infrared radiation of the infrared radiation source after the radiation has passed through the respiratory flow and the two the windows limiting the respiratory flow. At least one measuring transducer for the gas volume flow is arranged in the tubular housing outside of the beam path of the infrared radiation. The measuring transducer for the gas volume flow comprises two hot wires. The first hot wire is arranged in front of the beam path of the infrared radiation relative to the respiratory flow flowing past. The second hot wire is arranged behind the beam path of the infrared radiation relative to the respiratory flow flowing past. Both of the hot wires are directed substantially in parallel to the beam path of the infrared radiation.

An essential advantage of the respiratory flow sensor according to the invention is that the dead space volume formed by the sensor is markedly reduced due to the compact design, so that improved monitoring even of premature or newborn patients is possible during the mechanical respiration with respect to the composition and the flow parameters of the inspired and expired respiratory flow Another advantage of a special embodiment of the present invention with two hot wires as measuring transducers for the gas volume flow with an additional air resistance body in the vicinity of one hot wire is that the direction of the inspired or expired respiratory flow can thus be determined in addition to the amount of the gas volume flow. The distance between the two measurement points is preferably selected to be such that the infrared radiation passing through the respiratory flow passes undisturbed through the housing of the respiratory flow sensor, so that the high infrared radiation heat of the hot wires does not affect the infrared radiation radiated in for the concentration measurement from the outside of the housing. Further, the two measurements, namely, that of the gas volume flow and that of the concentration of gas components of the respiratory flow do not mutually affect one another because the infrared radiation of the hot wires does not reach the at least one infrared radiation detector, which is likewise arranged outside the housing.

It is particularly advantageous for this purpose for the hot wires to be directed in parallel to the infrared radiation passing through the housing.

Respiratory flow sensors according to the present invention are suitable for the FRC measurement, measuring a tracer gas instead of the $CO_2$.

The measuring transducer for the gas volume flow may be arranged on a measuring attachment that can be inserted into the housing of the respiratory flow sensor and which can be inserted into the housing essentially at right angles to the direction of flow of the respiratory flow and at right angles to the beam path of the infrared radiation.

At least one of the wires, e.g., the second hot wire may be arranged in the vicinity of a first air resistance body, so that a measured signal for the direction of the respiratory flow is detected due to the direction dependence of the cooling effect of the respiratory flow flowing past on the second hot wire The infrared sensor may have an U-shaped and one-piece design and may be pushed detachably over the housing and the windows of the respiratory flow sensor. The infrared radiation detector may be designed as a multispectral sensor for the measurement of a plurality of wavelength ranges of the infrared radiation.

The housing may essentially consist of a polysulfone or polycarbonate. The windows transparent to the infrared radiation may essentially consist of calcium fluoride and may also be formed of quartz glass, barium sulfide or polyester (for disposable articles).

The respiratory flow sensor in accordance with the invention may advantageously be used as part of a respiration process for the respiration of premature or newborn patients.

An exemplary embodiment of the present invention will be explained below on the basis of the figures.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which a preferred embodiment of the invention is illustrated.

DESCRIPTION OF THE PREFERRED EMBODIMENT

Figure 1:
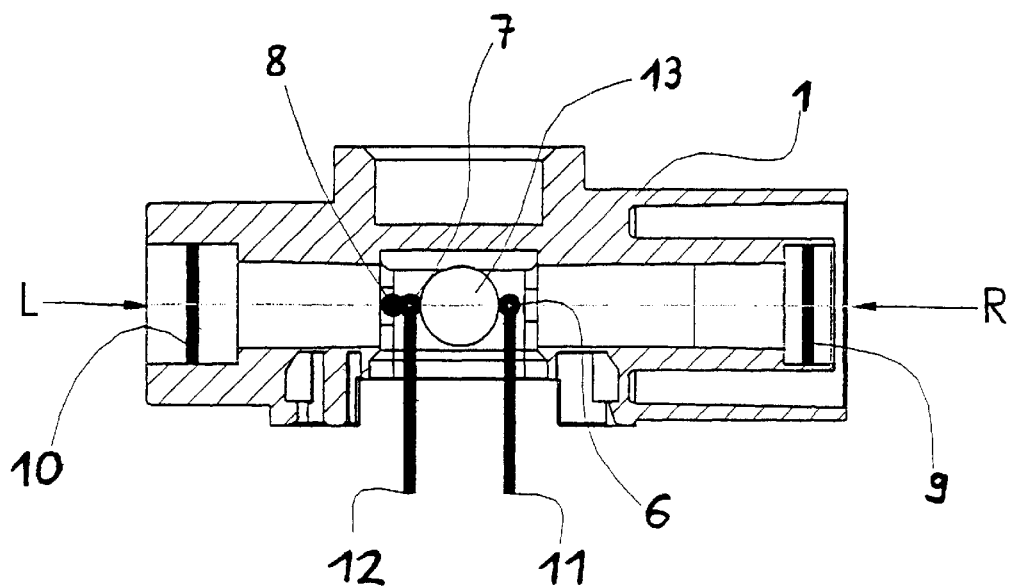
FIG. 1 is a longitudinal sectional view through a respiratory flow sensor according to the present invention.
Figure 2:
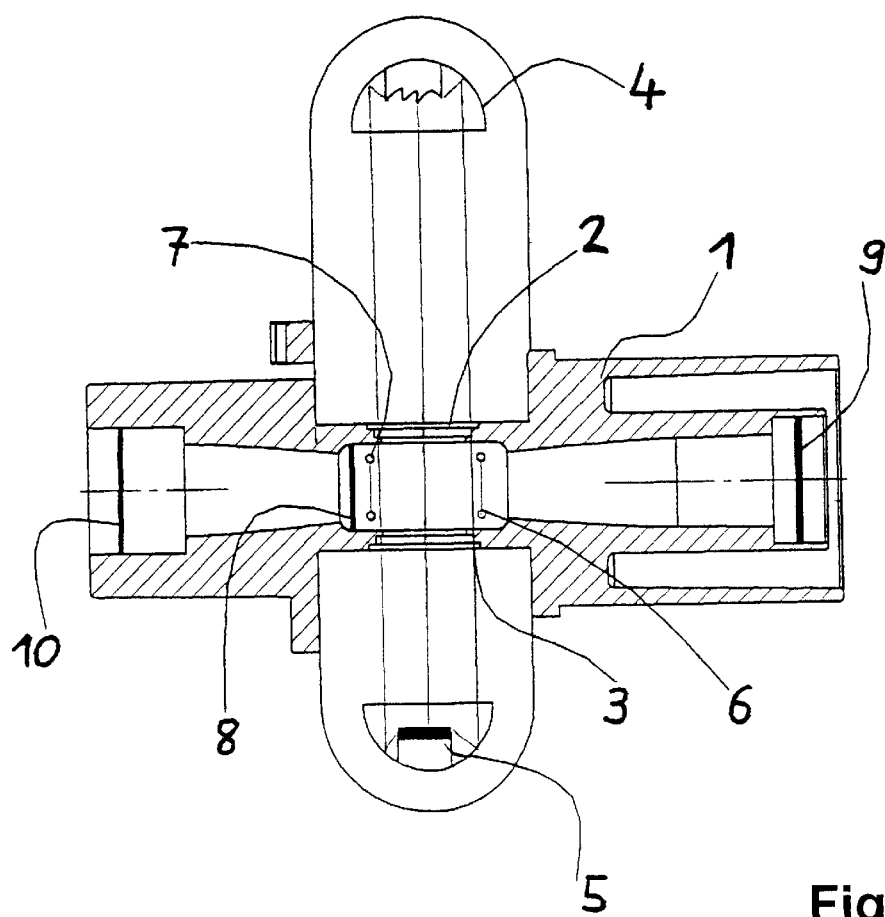
FIG. 2 is a second longitudinal sectional view through the respiratory flow sensor according to FIG. 1, but after rotation by 90° around the central longitudinal axis.

Referring to the drawings in particular, the invention comprises a respiratory flow sensor with a housing such as a tubular housing 1. The housing 1 is connected to a respiratory flow. The housing defines a space for the respiratory gas flow in the right direction R or and/or in the left direction L.

The tubular housing 1 is manufactured preferably in one piece from a suitable plastic, especially polysulfone or polycarbonate. At the left-hand and right-hand ends, the housing 1 is conical for standardized tube connections. The two windows 2, 3 are transparent to infrared radiation. These windows 2, 3 may be made of, e.g., quartz glass, barium sulfide or especially calcium fluoride or polyester (for disposable articles). The windows 2, 3 are inserted into a cross hole of the housing 1 opposite and at right angles to the direction of flow.

The infrared radiation passes through the windows 2, 3 and the respiratory flow from the infrared radiation source 4. The measured signal, weakened by the wavelength-dependent, gas-specific absorption of the infrared radiation, is received by at least one infrared radiation detector 5 and is an indicator of the concentration of a given gas, e.g., $CO_2$.

The infrared radiation source 4 forming the infrared sensor and the infrared radiation detector 5 are preferably designed in the form of a separate assembly unit that can be pushed over the housing 1.

The gas volume flow of the respiratory flow is determined by means of the two measuring transducers designed as hot wires 6, 7. The two hot wires 6, 7 are directed at right angles to the direction of flow of the respiratory flow and preferably in parallel to the direction of the infrared radiation passing through the housing 1 in order to interfere with the infrared optical measurement of the concentration and especially the infrared radiation detector 5 as little as possible.

To determine the direction of flow of the respiratory flow flowing by, an air resistance body 8 is located in the vicinity of the second hot wire 7, and the air resistance body affects the electric heating output of the second hot wire 7 differently than the first hot wire 6 depending on the direction of the respiratory flow, depending on whether the second hot wire 7 is located in the flow shadow of the air resistance body 8 during a flow from the left ("L" in FIG. 1) or it practically sends the same signal as the first hot wire 6 during flow from the right ("R" in FIG. 1).

To make the flow uniform, flow distributors 9, 10 are arranged at both inlets of the respiratory flow sensor. The flow distributors 9, 10 are designed, e.g., as metal screens.

Tests have shown that the diameter of the infrared radiation passing through the respiratory flow, schematically designated by 13 in FIG. 1, should be about 6 mm in order to obtain a reasonable signal-to-noise ratio. The diameter of the flow channel in the tubular housing 1 for the measurement of the gas volume flow was about 5 mm to obtain a sufficiently strong measured signal at low gas volume flows. The measured signals of the two hot wires 6, 7 are passed on to an evaluating unit via contacts 11, 12. The measured signals of the at least one infrared radiation detector 5 are also passed on to the evaluating unit. The evaluating unit may be designed, e.g., as a multispectral sensor for the measurement of the concentrations of different gas components, depending on the gas species-specific absorption wavelength to be measured.

The material of the two windows 2, 3 is selected depending on the gas species to be measured. For example, calcium fluoride is suitable for the wavelength spectrum of $CO_2$ (4.2 $\mu$m) and fluorides (8–12 $\mu$m).

While specific embodiments of the invention have been shown and described in detail to illustrate the application of the principles of the invention, it will be understood that the invention may be embodied otherwise without departing from such principles.

What is claimed is:

1. A respiratory flow sensor for the measurement of the gas volume flow and the concentration of gas components of the respiratory flow, the respiratory flow sensor comprising:

a tubular housing with two opposite windows arranged at right angles to the direction of flow, said windows being formed of a material transparent to infrared radiation;

an infrared sensor with a infrared radiation source and with least one infrared radiation detector, said infrared sensor being connected to the housing, the infrared radiation source irradiating one of the two windows of the housing and the infrared radiation detector receiving the infrared radiation of the infrared radiation source after the radiation has passed through the respiratory flow and the two the windows limiting the respiratory flow; and at least one measuring transducer for the gas volume flow arranged in said tubular housing outside the beam path of the infrared radiation, the measuring transducer for the gas volume flow comprising a first hot wire arranged in front of the beam path of the infrared radiation relative to the respiratory flow flowing past and a second hot wire arranged behind the beam path of the infrared radiation relative to the respiratory flow flowing past, each of said first hot wire and said second hot wire being directed substantially in parallel to the beam path of the infrared radiation.

2. A respiratory flow sensor in accordance with claim 1, wherein said at least one measuring transducer for the gas volume flow is arranged on a measuring attachment that can be inserted into the housing of the respiratory flow sensor and can be inserted into the housing essentially at right angles to the direction of flow of the respiratory flow and at right angles to the beam path of the infrared radiation.

3. A respiratory flow sensor in accordance with claim 1, further comprising a first air resistance body wherein said second hot wire is arranged in the vicinity of said first air resistance body so that a measured signal for the direction of the respiratory flow is detected due to the direction dependence of the cooling effect of the respiratory flow flowing past on the second hot wire.

4. A respiratory flow sensor in accordance with claim 1, wherein the infrared sensor has a U-shaped and one-piece design and is pushed detachably over the housing and the windows of the respiratory flow sensor.

5. A respiratory flow sensor in accordance with claim 1, wherein the infrared radiation detector is designed as a multispectral sensor for the measurement of a plurality of wavelength ranges of the infrared radiation.

6. A respiratory flow sensor in accordance with claim 1, wherein the housing essentially consists of a material selected from the group comprising polysulfones and polycarbonates.

7. A respiratory flow sensor in accordance with claim 1, wherein the windows transparent to the infrared radiation essentially consist of calcium fluoride.

8. A method of measuring gas volume flow and concentration of gas components of a measuring transducer, the method comprising the steps of:

providing a tubular housing with two opposite windows arranged at right angles to the direction of flow, said windows being formed of a material transparent to infrared radiation;

providing an infrared sensor with a infrared radiation source and with the infrared radiation source;

connecting the infrared sensor to the housing;

irradiating one of the two windows of the housing with the infrared radiation source;

receiving the infrared radiation at the of the infrared radiation source at the at least one infrared detector after the radiation has passed through the respiratory flow and the two the windows limiting the respiratory flow;

providing a measuring transducer for the gas volume flow comprising a first hot wire arranged in front of the beam path of the infrared radiation relative to the respiratory flow flowing past and a second hot wire arranged behind the beam path of the infrared radiation relative to the respiratory flow flowing past, each of said first hot wire and said second hot wire being directed substantially in parallel to the beam path of the infrared radiation; and measuring the gas flow with the measuring transducer.

9. A method in accordance with claim 8, wherein the respiratory flow is for a premature or newborn patient.

10. A flow sensor for measurement of a gas flow and concentration of gas components, the sensor comprising:

a housing defining a passage forming a flow path, said housing including two windows defining a portion of said passage, said two windows being arranged on diametrically opposite sides of said path, said windows being formed of a material transparent to infrared radiation;

an infrared radiation source connected to said housing, said infrared radiation source transmitting infrared radiation through one of said windows, then from said one window through said passage, and then from said passage through another of said windows;

an infrared radiation detector connected to said housing and receiving said infrared radiation of the infrared radiation source from said another window after said radiation has passed through said passage and said two windows;

a flow transducer arranged in said housing, said flow transducer including first and second hot wires arranged across said passage and spaced from said infrared radiation, said first and second hot wires being arranged on diametrically opposite sides of said infrared radiation.

11. A sensor in accordance with claim 10, wherein:

said first hot wire and said second hot wire are substantially in parallel to said infrared radiation passing through said passage.

12. A sensor in accordance with claim 11, wherein:

said first and second hot wires are arranged in a substantially identical plane.

* * * * *